(12) United States Patent
Medema et al.

(10) Patent No.: US 6,747,556 B2
(45) Date of Patent: Jun. 8, 2004

(54) METHOD AND SYSTEM FOR LOCATING A PORTABLE MEDICAL DEVICE

(75) Inventors: Douglas K. Medema, Everett, WA (US); William E. Saltzstein, Woodinville, WA (US); Robert A. Niskanen, Seattle, WA (US); Richard C. Nova, Kirkland, WA (US)

(73) Assignee: Medtronic Physio-Control Corp., Redmond, WA (US)

( * ) Notice: Subject to any disclaimer, the term of this patent is extended or adjusted under 35 U.S.C. 154(b) by 0 days.

(21) Appl. No.: 09/919,783

(22) Filed: Jul. 31, 2001

(65) Prior Publication Data

US 2003/0025602 A1 Feb. 6, 2003

(51) Int. Cl.⁷ .................................................. G08B 1/08
(52) U.S. Cl. ......................... 340/539.12; 340/539.1; 340/539.13; 340/286.07; 340/7.1
(58) Field of Search ........................ 340/539.1, 539.12, 340/539.13, 7.1, 7.21, 7.58, 286.07, 539.32

(56) References Cited

U.S. PATENT DOCUMENTS

| | | |
|---|---|---|
| 3,724,455 A | 4/1973 | Unger |
| 5,003,984 A | 4/1991 | Muraki et al. |
| 5,208,756 A | 5/1993 | Song |
| 5,218,367 A | 6/1993 | Sheffer et al. |
| 5,228,449 A | 7/1993 | Christ et al. |
| 5,304,209 A | 4/1994 | Adams et al. |
| 5,348,008 A | 9/1994 | Bornn et al. |
| 5,354,315 A | 10/1994 | Armstrong |
| 5,512,908 A | 4/1996 | Herrick |
| 5,549,653 A | 8/1996 | Stotts et al. |
| 5,555,286 A | 9/1996 | Tendler |
| 5,593,426 A | 1/1997 | Morgan et al. ................. 607/5 |
| 5,607,459 A | 3/1997 | Paul et al. |
| 5,609,614 A | 3/1997 | Stotts et al. |
| 5,609,615 A | 3/1997 | Sanders et al. |
| 5,626,630 A | 5/1997 | Markowitz et al. |
| 5,630,209 A | 5/1997 | Wizgall et al. ............. 455/521 |
| 5,647,379 A | 7/1997 | Meltzer |
| 5,650,770 A | 7/1997 | Schlager et al. |
| 5,657,487 A | 8/1997 | Doner |
| 5,669,391 A | 9/1997 | Williams |
| 5,683,432 A | 11/1997 | Goedeke et al. |
| 5,687,734 A | 11/1997 | Dempsey et al. |

(List continued on next page.)

FOREIGN PATENT DOCUMENTS

| | | |
|---|---|---|
| DE | 4441907 A1 | 6/1995 |
| DE | 19836118 A1 | 4/1999 |
| GB | 2 285 135 | 6/1995 |

OTHER PUBLICATIONS

Bellsouth, "Simplified Wireless E911 Call Flow in 2001 with Phase II," http://www.bellsouthcorp.com/issues/911/chart9.html, 1997 (Apr. 4, 2000).

(List continued on next page.)

Primary Examiner—Daryl Pope
(74) Attorney, Agent, or Firm—Shumaker & Sieffert, P.A.

(57) ABSTRACT

The invention provides a wireless automatic location identification (ALI) capable system (10), including a medical device (12) having a wireless data communicator (14), a wireless communication network (16), and a remote locating service (18) for remotely locating and monitoring one or more medical devices over the wireless communication network. When the medical device is linked to the remote locating service over the communication network, the ALI-capable system identifies the location of the medical device and relays the location information to the remote locating service. The system permits reliable determination of the location of the medical device wherever the medical device is situated. The medical device may further be configured to transmit signals indicative of its status, condition, or self-test results, to the remote locating service. This feature allows the remote locating service to centrally monitor the status or condition of a plurality of medical devices.

38 Claims, 5 Drawing Sheets

U.S. PATENT DOCUMENTS

| | | |
|---|---|---|
| 5,701,328 A | 12/1997 | Schuchman et al. |
| 5,709,712 A | 1/1998 | Paul et al. |
| 5,712,619 A | 1/1998 | Simkin |
| 5,720,770 A | 2/1998 | Nappholz et al. |
| 5,731,757 A | 3/1998 | Layson, Jr. |
| 5,732,354 A | 3/1998 | MacDonald |
| 5,752,976 A | 5/1998 | Duffin et al. |
| 5,766,232 A | 6/1998 | Grevious et al. |
| 5,767,788 A | 6/1998 | Ness |
| 5,782,878 A | 7/1998 | Morgan et al. |
| 5,835,907 A | 11/1998 | Newman |
| 5,840,020 A | 11/1998 | Heinonen et al. |
| 5,843,139 A | 12/1998 | Goedeke et al. |
| 5,872,505 A | 2/1999 | Wicks et al. |
| 5,873,040 A | 2/1999 | Dunn et al. |
| 5,874,897 A | 2/1999 | Klempau et al. |
| 5,876,353 A | 3/1999 | Riff |
| 5,904,708 A | 5/1999 | Goedeke |
| 5,921,938 A | 7/1999 | Aoyama et al. |
| 5,926,133 A | 7/1999 | Green, Jr. |
| 5,931,791 A | 8/1999 | Saltzstein et al. |
| 5,937,355 A | 8/1999 | Joong et al. |
| 5,959,529 A | 9/1999 | Kail, IV |
| 5,960,337 A | 9/1999 | Brewster et al. |
| 5,970,414 A | 10/1999 | Bi et al. |
| 5,971,921 A | 10/1999 | Timbel |
| 5,987,329 A | 11/1999 | Yost et al. |
| 6,002,936 A | 12/1999 | Roel-Ng et al. |
| 6,016,477 A | 1/2000 | Ehnebuske et al. |
| 6,021,330 A | 2/2000 | Vannucci |
| 6,021,371 A | 2/2000 | Fultz |
| 6,026,304 A | 2/2000 | Hilsenrath et al. |
| 6,026,305 A | 2/2000 | Salinger et al. |
| 6,028,537 A | 2/2000 | Suman et al. |
| 6,034,635 A | 3/2000 | Gilhousen |
| 6,046,687 A | 4/2000 | Janky |
| 6,047,182 A | 4/2000 | Zadeh et al. |
| 6,386,882 B1 * | 5/2002 | Linberg ..................... 434/262 |

OTHER PUBLICATIONS

TruePosition, Inc., TDOA Overview, "Time difference of arrival technology for locating narrowband cellular signals," http://www.trueposition.com/tdoa.htm, 1998–2000, (Apr. 4, 2000).

Xypoint Corporation, "Model W E9–1–1 Model Legislation," http://www.xypoint.com/we911/legislation/modelact.html, 1999, (Apr. 4, 2000).

Xypoint Corporation, "FCC Final Order Docket CC 94–102, Part 1," http://www.xypoint.com/we911/legislation/fccorder1.html, 1999, (Apr. 4, 2000).

* cited by examiner

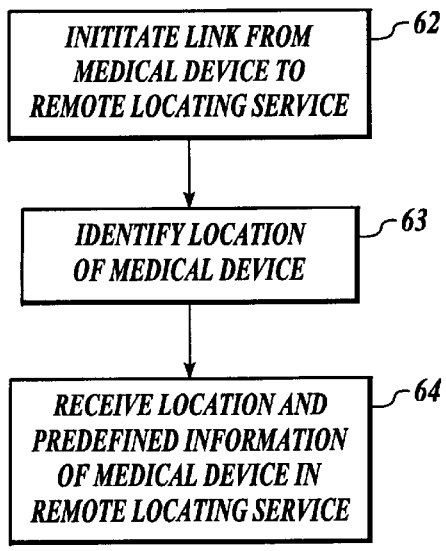
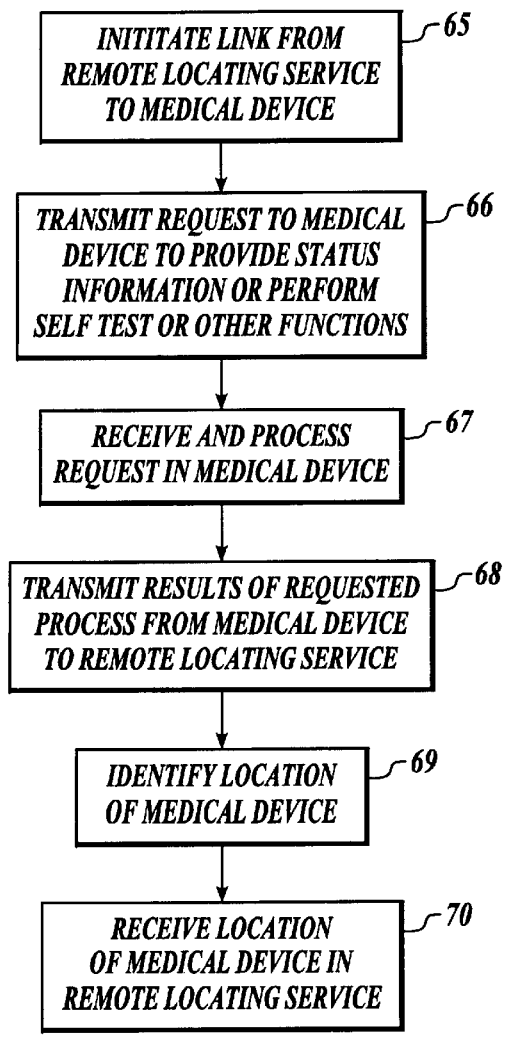

METHOD AND SYSTEM FOR LOCATING A PORTABLE MEDICAL DEVICE

FIELD OF THE INVENTION

The present invention is related to communication systems for use with a medical device and, more particularly, to wireless communication systems for automatically identifying the location of a medical device.

BACKGROUND OF THE INVENTION

The current trend in the medical industry is to make life-saving portable medical devices, such as automated external defibrillators (AEDs), more widely accessible. As the availability of portable medical devices continues to increase, more places will have these devices for use in emergency situations. However, this increase also comes with the heightened likelihood that these portable medical devices will be used by people without medical training. The advantage of having a life-saving medical device immediately available to a lay person is then fully realized when use of the device is followed by professional emergency medical care. For AEDs, the increase in survival rate made possible by early defibrillation is enhanced when advanced life support (ALS) providers can arrive on the scene in a timely fashion. Indeed, the American Heart Association (AHA) recommends that early defibrillation be followed by care provided by persons trained in ALS. This presents two requirements for AEDs: (1) ALS providers must be promptly notified that an AED is being used; and (2) ALS providers must be given the location of the AED.

Previous attempts to meet these two requirements have included the use of a global positioning system (GPS) receiver to obtain the AED's location and a cellular telephone to give the location to ALS providers. The GPS receiver, when fully functional, is advantageous because often times the person making a call to ALS providers is not aware of, or mistaken about, his exact location, especially in case of emergency. The problem is that current GPS receivers do not work well in metal buildings, or "urban canyons," due to signal interference and blockage. Thus, although a cellular telephone could be used to alert ALS providers that an AED is being used, it cannot give the device's location to ALS providers when the device is used in certain unfavorable locations.

SUMMARY OF THE INVENTION

The present invention provides a system and method for reliably locating a portable medical device, such as an AED, by utilizing wireless automatic location identification (ALI) technologies that overcome the problems associated with automatically providing the location of a medical device.

Specifically, the invention provides a wireless ALI-capable system, including a medical device having a wireless data communicator, such as a cellular phone. The ALI-capable system further includes a wireless communication network and a remote locating service for remotely locating and monitoring one or more medical devices over the wireless communication network. When the medical device is linked to the remote locating service over the communication network, the ALI-capable system identifies the location of the medical device and relays the location information to the remote locating service. The term ALI refers to the location identification capability in compliance with the wireless Enhanced 911 standard prescribed by the United States Federal Communications Commission ("the wireless E911 standard"). The wireless E911 standard mandates that cellular phone service providers within the United States provide the capability to locate the position of a cellular phone making an emergency (911) call within the provider's system. The term ALI, as used in the present description, encompasses such location identification capability as applied to all calls placed to any numbers, not limited to emergency calls nor limited to calls placed only in the United States. The ALI capability may be based on handset-based technologies, network-based technologies, or a combination of handset-based and network-based technologies. Using the ALI-capable system of the present invention, an operator of the remote locating service can reliably identify the location of the medical device calling the remote locating service, even when the medical device is placed in unfavorable locations, such as within urban canyons.

In one embodiment, a medical device of the ALI-capable system is configured to automatically link itself to the remote locating service over the network upon occurrence of a predetermined triggering event. For example, the medical device may be configured to establish a link upon activation (turning on) of the medical device. When the medical device is implemented as a defibrillator, the defibrillator may be configured so that application of electrodes to a patient will trigger initiation of a link. Any other events associated with the operation of the medical device can be used as a link-triggering event. This feature is advantageous in case of emergency deployment of a defibrillator, because use of a defibrillator can then be immediately reported to an emergency response central dispatch (where the remote locating service is situated) and followed up by paramedics trained in advanced life support (ALS) procedures. Consequently, this embodiment meets both of the requirements discussed in the background section above: (1) ALS providers must be promptly notified that an AED is being used; and (2) ALS providers must be given the location of the AED.

In another embodiment, a medical device of the ALI-capable system is configured to transmit various information to the remote locating service over the network, such as the status or condition of the medical device (battery level, etc.), self-test results, or even physiological data of a patient being treated with the medical device. This may be performed upon inquiry from the remote locating service, periodically, or even automatically. The transmitted information may then be received by the remote locating service for display or further processing. This feature allows an operator at the remote locating service to not only identify the location of the medical device but also monitor the medical device itself or events occurring in association with the medical device at the remote emergency site. A user of the medical device and an operator of the remote locating service can also communicate with each other verbally, via text messaging, and/or graphical messaging in conventional manners.

In yet another embodiment, the ALI-capable system is suited for centrally monitoring a plurality of medical devices. Specifically, a medical device of the ALI-capable system is configured to transmit various information indicative of the status, condition, or self-test results of the medical device to the remote locating service over the network. The transmission may be programmed to occur upon inquiry from the remote locating service, periodically, or even automatically upon detection of certain triggering events, such as malfunctioning of the device or deployment (turning on) of the device. Any detected triggering event will then be relayed to the remote locating service. Additionally, the transmission of information may be programmed to occur according to a predetermined schedule stored in the medical device. For example, the medical device may be configured to notify the remote locating service that a component of the medical device has expired or is nearing its expiration, or that an owner or designated operator of the medical device needs to be retrained in the use and operation of the medical device. Accordingly, an operator at the remote locating service may receive such information regarding the status/condition of the medical device. As before, the operator also receives the location information of the medical device according to the ALI-capable system of the present invention. Thus, the operator can take an appropriate action, for example, by sending a service agent to the medical device to perform necessary servicing.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 6 is a flow diagram illustrative of the operation of the ALI-capable system of FIG. 1, according to another embodiment of the present invention; and FIG. 7 is a flow diagram illustrative of the operation of the ALI-capable system of FIG. 1, according to yet another embodiment of the present invention.

DETAILED DESCRIPTION OF THE PREFERRED EMBODIMENT

Figure 1:
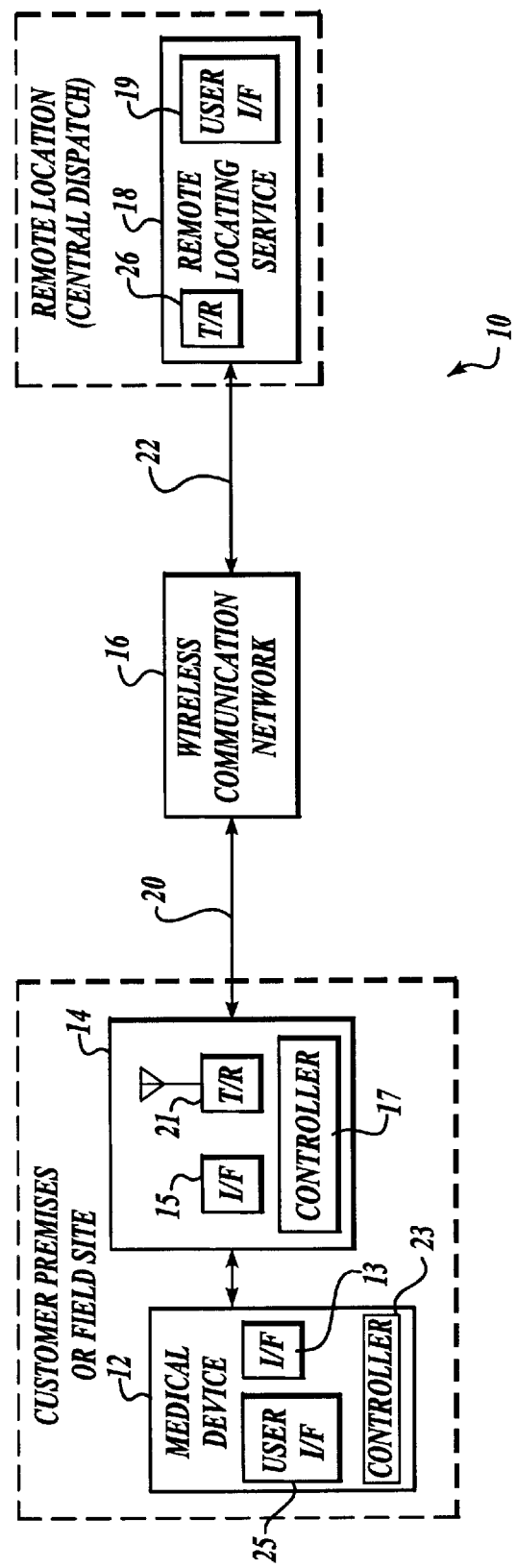
FIG. 1 is a block diagram illustrating a wireless automatic location identification (ALI) capable system for locating a portable medical device, according to one embodiment of the present invention.

FIG. 1 is a diagram illustrative of a wireless automatic location identification (ALI) capable system 10 for locating a portable medical device, according to one embodiment of the present invention. The ALI-capable system 10 includes a medical device 12 having a wireless data communicator 14; a wireless communication network 16; and a remote locating service 18 having a user interface 19. Although only one medical device 12 is shown in FIG. 1, it will be appreciated that the remote locating service 18 can locate and further communicate with a relatively large number of medical devices (not shown) when linked to those medical devices.

The medical device 12 includes a controller 23, a user interface 25, and whatever circuitry necessary for the operation of the medical device 12. In addition, the medical device 12 includes a data communication interface 13. Similarly, the wireless data communicator 14 includes a data communication interface 15. Accordingly, interface 13 and interface 15 support communication therebetween. As nonlimiting examples, the interfaces 13 and 15 may be RS-232 bus connections, radio frequency (RF) interfaces (e.g., Bluetooth), or infrared (IR) interfaces. In this embodiment, the wireless data communicator 14 further includes a controller 17 and a transmission/reception module 21. The controller 17 includes a standard processor and associated memory (not shown) and is configured to communicate data between the medical device 12 and the wireless communication network 16. The transmission/reception module 21 serves as a processing interface between the controller 17 and the communication network 16, and may include radiofrequency circuits comprising, for example, an encoder, modulator, decoder, demodulator, and antenna.

The wireless communication network 16 utilizes any one of a variety of wireless communication mediums and/or communication methods to transfer data. Examples include, but are not limited to, wireless telephony, including analog cellular, digital personal communication service ("PCS"), short message service ("SMS"), and wireless application protocol ("WAP"). Other suitable wireless communication mediums/methods include wireless digital data networks, such as 802.11 wireless LAN ("WLAN"), two-way paging networks, specialized mobile radio systems, infrared, and non-licensed ISM-service communication link, such as the Bluetooth protocol. Further wireless communication methods include Internet protocol ("IP") addressing. Accordingly, the wireless data communicator 14 can be any device that communicates with the chosen wireless communication network 16 through a wireless channel 20. For example, the wireless data communicator 14 may be a cellular phone, pager, personal digital assistant, or PCS handset. The wireless communication network 16 may also include a network which is in part a wired network. For example, the wireless communication network 16 may include the standard Public Switched Telephone Network (PSTN) with which the wireless data communicator 14 interfaces. The wireless communication network 16 further communicates with the remote locating service 18 through a landline or wireless channel 22. In one embodiment where the wireless communication network 16 includes the PSTN, the remove locating service 18 may be wired to the PSTN. In another embodiment where the wireless communication network 16 is a cellular telephone system, the channels 20 and 22 may be standard cellular telephone connections interfaced with the transmitter/receiver modules 21 and 26, respectively, of the wireless data communicator 14 and the remote locating service 18.

Figure 2:
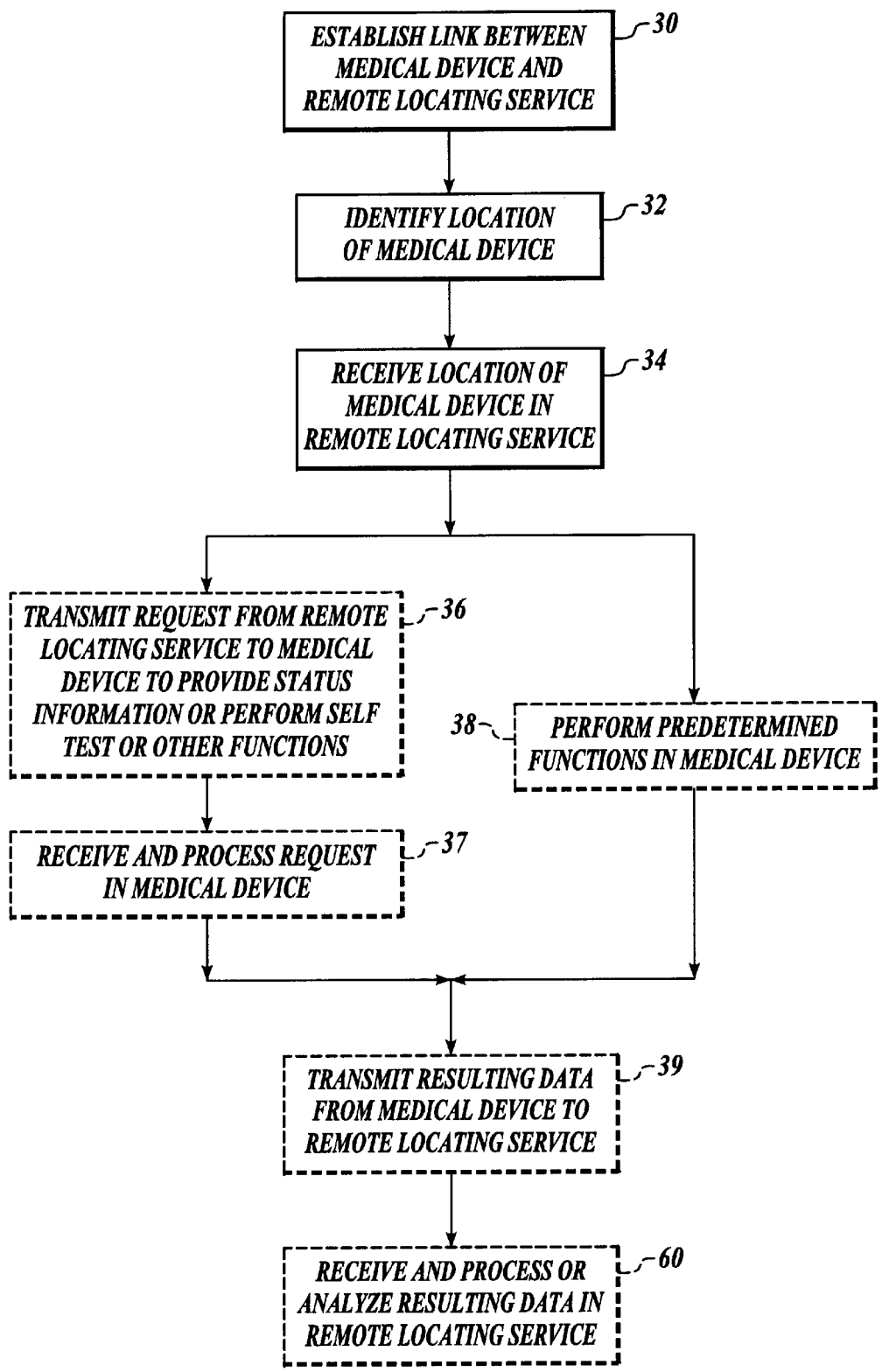
FIG. 2 is a flow diagram illustrative of the operation of the ALI-capable system of FIG. 1, according to one embodiment of the present invention.

FIG. 2 is a flow diagram illustrative of the operation of the wireless ALI-capable system 10 according to one embodiment of the present invention. Referring to FIGS. 1 and 2, the wireless ALI-capable system 10 operates as follows. In block 30, a communication link is established between the medical device 12, specifically the wireless data communicator 14 of the medical device 12, and the remote locating service 18 over the wireless communication network 16. As indicated by the dashed lines in FIG. 1, the medical device 12 can be located at the user's (patient's) premises or at a field site, for example, a public gathering place where a portable medical device is deployed in case of emergency. The remote locating service 18 can be located at a central dispatch, i.e., a public safety answering point, which is a termination point of emergency calls (e.g., 911 calls in the United States). Alternatively, the remote locating service 18 can be located at an emergency medical care facility or any other remote site. The communication link may be initiated by the medical device 12, for example, by the user of the medical device 12 calling a number (perhaps an emergency call number) associated with the remote locating service 18 using the wireless data communicator 14. In other situations, the communication link may be initiated by the remote locating service 18, as more fully described below.

In block 32, the wireless ALI-capable system 10 identifies the location of the medical device 12. In the present description, the term ALI (automatic location identification) is used to refer to the location identification capability in compliance with the wireless Enhanced 911 standard prescribed by the United States Federal Communications Commission (hereinafter "the wireless E911 standard"). Specifically, pursuant to the wireless E911 standard, cellular phone service providers within the United States must provide by Oct. 1, 2001 the capability to locate the position of a cellular phone making an emergency (911) call within the provider's system, and this capability is called ALI. ALI may be accomplished using handset-based technologies or solutions, e.g., a cellular phone equipped to self-identify its location, which may incorporate a global positioning system (GPS) receiver. In this embodiment, the data communicator 14 (handset) is adapted to identify the location of the medical device 12. Alternatively, ALI may be accomplished using network-based technologies or solutions, wherein the location of a data communicator 14 is identified based on a communication link connecting the data communicator 14 and the remote locating service 18 over the network 16. For example, certain cellular phone systems track the strength, the angle, and the arrival time difference of transmission signals for determining a cell phone's location, using time difference of arrival (TDOA) technology or timing advance (TA) location measurement technology. In this embodiment, the location of the medical device 12 is identified by the overall communication network 16, perhaps at its base station, and the identified location may or may not be relayed to the data communicator 14. Further alternatively, ALI may be based on a combination of both handset-based technologies and network-based technologies. For handset-based solutions, the wireless E911 standard requires that a call location be identified within 50 meters for 67% of calls, and 150 meters for 95% of calls. For network-based solutions, a call location must be identified within 100 meters for 67% of calls, and within 300 meters for 95% of calls. A variety of ALI techniques are under development and/or available, some of which can be found in U.S. Pat. Nos. 5,926,133; 5,970,414; 5,987,329; 6,002,936; 6,021,330; 6,026,304; and 6,026,305, all incorporated herein by reference. Accordingly, the term "wireless ALI-capable system," as used in the present description, refers to any wireless system that meets the wireless E911 standard regardless of particular technologies used to meet the standard.

It should be appreciated that those skilled in the art can readily apply any ALI technologies developed to meet the wireless E911 standard in countries other than the United States, where emergency medical service phone numbers are other than 911. In other words, a wireless ALI-capable system of the present invention is equally implementable in countries other than the United States without undue experimentation, and therefore is intended to encompass all such ALI-capable systems applied in various networks in various countries.

It should further be appreciated by those skilled in the art that, although the wireless E911 standard relates to only wireless 911 emergency calls placed to an emergency response central dispatch, any ALI-capable system can be equally applied to determine the location of a data communicator, such as a cellular phone, placing a call to any number. Therefore, the term "wireless ALI-capable system" as used in the present invention encompasses all such systems, wherein the remote location service 18 is not necessarily situated at the emergency response central dispatch and associated with an emergency call number. For example, the remote locating service 18 may be operated by a person, perhaps a person associated with the manufacturer of medical devices, in charge of centrally monitoring and maintaining a plurality of medical devices, as more fully described below.

Finally, in block 34, the location of the medical device 12 identified by the wireless ALI-capable system 10 is received in the remote locating service 18, and preferably displayed on the user interface 19 (FIG. 1). As described earlier, depending on a particular embodiment of the ALI-capable system 10, the location may be identified by the data communicator 14 (handset) itself, by the overall communication network 16, or by a combination of the data communicator 14 and the communication network 16. In any event, the identified location is then received in the remote locating service 18. When the remote locating service 18 is situated at an emergency response central dispatch, the central dispatch may use the identified location information to, for example, send paramedics to the identified location or advise the medical device's user of the medical facility that is nearest to the identified location. Optional blocks 36–60 in FIG. 2 will be described later.

Figure 3:
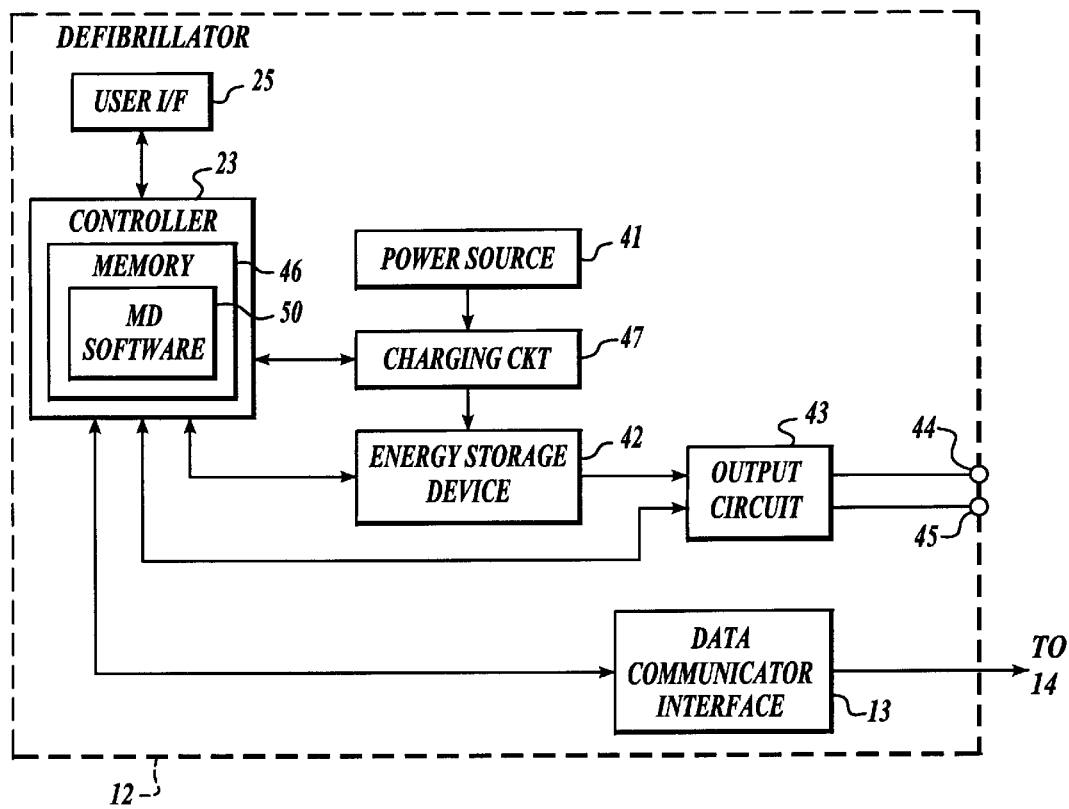
FIG. 3 is a block diagram of a portable medical device comprising a defibrillator.

In one actual embodiment of the present invention, the medical device 12 is a defibrillator. FIG. 3 is a block diagram of such a defibrillator. Although a defibrillator is used in this embodiment, in light of this disclosure, those skilled in the art will be able to implement other embodiments using other types of medical equipment without undue experimentation. The defibrillator 12 includes a controller 23, a power source 41, a charging circuit 47, an energy storage device 42, an output circuit 43, output electrodes 44 and 45, a data communicator interface 13, and a user interface 25.

The controller 23 includes a microprocessor (not shown) such as, for example, a model 68332 available from Motorola, along with a memory 46. Preferably, the memory 46 includes random-access memory such as a DRAM (dynamic random access memory) or SRAM (static random access memory), and nonvolatile memory such as an EEPROM (electrically erasable programmable read-only memory). The EEPROM can be used to store software programs executed by the microprocessor (not shown), such as medical device software 50 that controls the operation of the medical device 12, as will be described in detail below. In addition, the EEPROM allows the stored software programs to be remotely updated.

The power source 41 is implemented with a battery, such as a LIFEPAK®500 battery available from Medtronic Physio-Control Corp. of Redmond, Wash. The charging circuit 47 is coupled to the power source 41. The energy storage device 42 is coupled to the charging circuit 47 and is implemented with a capacitor with a capacitance of about 190–200 µF. The output circuit 43 is coupled to the energy storage device 42 and is implemented in an H-bridge configuration, which facilitates generating biphasic defibrillation pulses. In operation, as well known in the art, under the control of the controller 23, the charging circuit 47 transfers energy from the power source 41 to the energy storage device 42, and the output circuit 43 transfers energy from the energy storage device 42 to the electrodes 44, 45. The data communicator interface 13 is implemented with a standard data communication port. The user interface 25 is implemented with conventional input/output devices, including, for example, a display, speaker, input keys, and microphone.

In one embodiment, the controller 23, the power source 41, the charging circuit 47, the energy storage device 42, the output circuit 43, the electrodes 44 and 45, and the user interface 25 are the similar to those used in a LIFEPAK®500 AED available from Medtronic Physio-Control Corp. That is, the hardware aspect of the medical device 12 is similar to a LIFEPAK®500 AED with the addition of the interface 13 to the wireless data communicator 14 along with suitable software programming stored in the memory 46.

In FIGS. 1 and 3, the medical device 12 and the wireless data communicator 14 are illustrated to be separate components coupled together via the respective interfaces 13 and 15. This embodiment is advantageously used to upgrade existing medical devices that have a communication port interface 13 by simply coupling a separate data communicator 14 thereto. It should be understood, though, that in another embodiment the medical device 12 may integrally incorporate the data communicator 14. In this embodiment, the controller 23 of the medical device 12 and the controller 17 of the wireless data communicator 14 will be consolidated, as will be apparent to those skilled in the art.

There are various types of defibrillators. For example, a fully automatic AED monitors and analyzes electrocardiogram (ECG) of a patient and, based on the ECG analysis, automatically delivers a defibrillation shock to the patient through electrodes. Most AEDs, on the other hand, are semiautomatic in the sense that once the ECG analysis indicates that defibrillation is recommended, a user is prompted to manually trigger delivery of a defibrillation shock to the patient. In addition, there is a manual defibrillator, which monitors and displays the patient's ECG. An operator of the defibrillator must then analyze the ECG and decide whether or not to apply a defibrillation shock to the patient. Therefore, the term defibrillator as used in the present description is intended to encompass various types of defibrillators.

Figure 4:
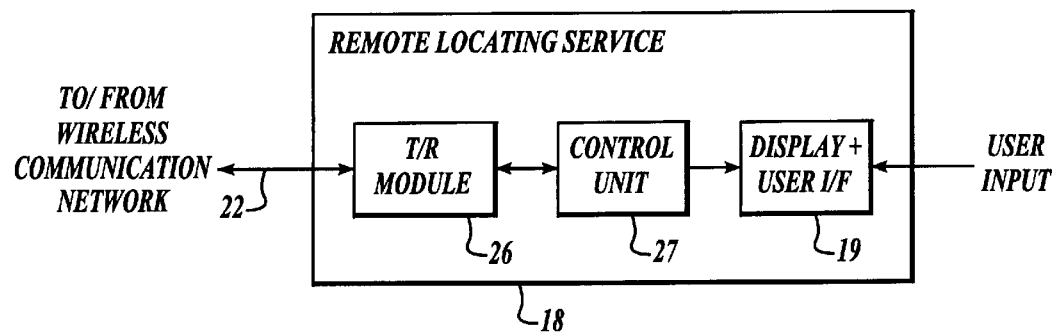
FIG. 4 is a block diagram illustrative of the remote locating service in FIG. 1, according to one embodiment of the present invention.

FIG. 4 is a block diagram illustrative of the remote locating service 18 (FIG. 1) according to one embodiment of the present invention. In this embodiment, the remote locating service 18 includes the transmission/reception module 26 (may be interfacing with a wired network or a wireless network), a control unit 27, and the user interface 19 including conventional input/out devices such as a display, speaker, input keys, and microphone. The control unit 27 includes a standard processor and associated memory (not shown), and is configured to perform various functions. For example, the control unit 27 is configured to receive and display the location of a medical device as identified by the ALI-capable system on the display 19, or to directly communicate with the medical device 12, as more fully described below in conjunction with FIGS. 2 and 5–7.

Referring back to FIG. 2, optionally, following block 34, the remote locating service 18 may be configured to transmit a request signal addressed to the linked medical device 12 in a block 36. The request signal includes, for example, instructions (or codes representing instructions) for the medical device 12 to provide status and condition information (e.g., battery charge level, configuration parameters), perform self-test (e.g., battery age self-test), change the configuration (i.e., update the software) of the medical device 12, or obtain patient data (e.g., ECG data). The user interface 19 of the remote locating service 18 (FIG. 4) may be used to initiate a request signal and any associated data to the medical device 12. This feature may be advantageous, for example, in a case when the remote locating service 18 located at an emergency medical facility has received a call from the medical device 12 and personnel at the facility wish to ensure that the medical device 12 is fully operational and/or fully updated. As another example, the request signal may instruct the medical device 12 to send physiological data of a patient detected by the medical device 12 to the remote locating service 18. This feature will allow emergency personnel stationed at the remote locating service 18 to monitor the condition of the patient.

In a next block 37, the medical device 12 receives the request signal and extracts its instructions. The medical device 12 then performs the extracted instructions. For example, the medical device 12 may obtain the requested status or condition information or perform self-tests or a software update. Alternatively or additionally, the medical device 12 obtains physiological data of a patient being treated with the medical device 12. Next, in block 39, the medical device 12 transmits the resulting data of the requested process to the remote locating service 18. The transmitted resulting data may be the requested status or condition information, self-test results, a confirmation that software update has been completed, or physiological data of a patient detected by the medical device 12.

Finally in a block 60, the resulting data transmitted from the medical device 12 is received and processed in the remote locating service 18. For example, the data may be displayed on the user interface 19 of the remote locating service 18. A person at the remote locating service 18 can then analyze the displayed information and take appropriate action. Alternatively, the remote locating service 18 may be configured with a computer programmed to analyze the information. In one example, the return data may contain the results of a self-test conducted by the medical device 12, indicating that the medical device 12 has failed the self-test. The person at the remote locating service 18 can then instruct the user of the medical device 12 to go to the nearest medical facility or to the nearest medical device that is predetermined to be fully functional. Such instructions can be communicated to the user of the medical device 12 verbally, with text messaging, and/or with graphic messaging (mapping) in conventional manners.

Referring back to the block 36, additionally, the remote locating service 18 may transmit a request signal to the medical device 12 to perform various other functions. As one example, a request signal may include instructions directing the medical device 12 to perform functions to assist a person in the vicinity of the medical device 12 to easily locate the medical device 12. This feature will be advantageous, for example, in a case when an emergency response central dispatch has received an emergency call from a person not having a functional medical device and wishes to direct the person to the nearest medical device 12. In this case, the central dispatch preferably has recorded the locations of a plurality of medical devices 12 strategically placed within its jurisdiction. Upon receiving an emergency call from a person not having a medical device and establishing the caller's location, via the caller himself and/or via his ALI-capable phone, the central dispatch identifies and, using the remote locating service 18, calls the medical device 12 that is nearest to the caller's location to establish a communication link (block 30 of FIG. 2). The central dispatch then verifies the location of the medical device 12 (blocks 32 and 34), and instructs the emergency caller where to locate the medical device 12. The location instructions may be transmitted verbally, with text messaging, and/or with graphic messaging (mapping) in conventional manners. Alternatively or additionally, when the phone number of the emergency caller is known, the central dispatch may send a request signal to the medical device 12 to directly call the emergency caller's phone to transmit location instructions of the medical device 12 (block 36). At the same time, the central dispatch may send a request signal to the medical device 12 to emit an audible location alert (block 36). The medical device 12 receives and processes this request signal, emitting an audible location alert via its user interface 25 (speaker) to assist the emergency caller in finding the medical device 12 (block 37).

Alternatively, the central dispatch may send a signal indicative of the location of the emergency (i.e., the location of the caller without a functional medical device) to the medical device 12 (block 36). Thereupon, the medical device 12 is activated to audibly announce and/or graphically display the location of the emergency via its user interface 25 (block 37). A third party at the vicinity of the medical device 12 can then verify the emergency location and take the medical device 12 to the emergency location.

Alternatively to the steps 36 and 37, the medical device 12 may perform in a block 38 predetermined functions without first receiving a request signal from the remote locating service 18. For example, the medical device 12 may obtain various status/condition information of the medical device 12, or perform self-tests or software updates. Alternatively or additionally, the medical device 12 may be configured to automatically prepare physiological data (e.g., ECG data) measured by the medical device 12 for transmission. The performance of various functions in block 38 may be automatic, for example, upon establishment of a link between the medical device 12 and the remote locating service 18, or may be semiautomatic, for example, upon receiving input from the user of the medical device 12. Thereafter, as before, in the block 39 the resulting data from the block 38 are transmitted to the remote locating service 18. Then in the block 60, the resulting data are displayed or otherwise processed and may further be analyzed in the remote locating device 18.

Figure 5:
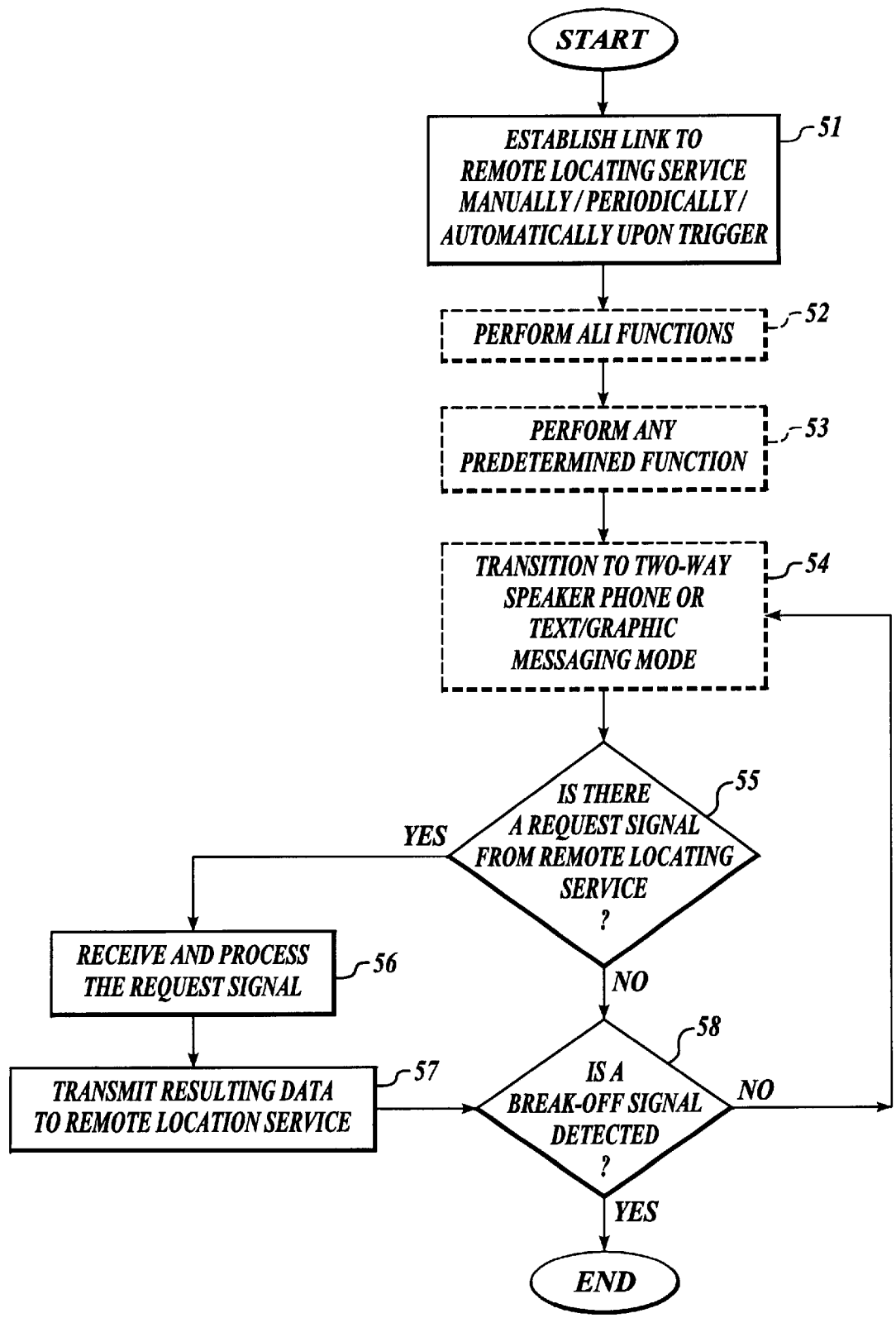
FIG. 5 is a flow diagram illustrative of the operation of medical device software included in the medical device of FIG. 1, according to one embodiment of the present invention.

Now that the operation of ALI-capable system 10 has been described, the operation of the medical device 12 itself capable of being automatically located will be discussed in greater detail. FIG. 5 is a flow diagram illustrative of the operation of the microprocessor (not shown) of the medical device 12 in accordance with the medical device software 50 included in the memory 46 (FIG. 3) according to one embodiment of the present invention. In block 51, the medical device 12, via the wireless data communicator 14, establishes a link to the remote locating service 18. This may be done manually, for example by the user of the medical device 12 dialing a number associated with the remote locating service 18. Alternatively, the link to the remote locating service 18 may be established periodically according to a predetermined schedule. This feature may be advantageous, for example, where one or more medical devices are centrally monitored by the remote locating service 18, as more fully described below. Further alternatively, a link to the remote locating device 18 may be established automatically upon occurrence of any triggering event associated with the medical device 12. For example, the medical device 12 may be configured to initiate a link to the remote locating service 18 when the medical device is activated (i.e., turned on or removed from a base station). When the medical device 12 comprises a defibrillator, a link may be initiated upon application of defibrillation electrodes (44 and 45 in FIG. 3) on the patient. The automatic link establishment feature is advantageous in case of emergency deployment of the medical device 12, for example, a defibrillator, because use of a defibrillator should be immediately reported to the emergency response central dispatch and followed up by application of advanced life support (ALS) procedures by paramedics. Any other events associated with the operation of the medical device 12 can be used as a link-triggering event, which will be described in further detail below in association with FIG. 6. Additionally, the medical device 12 is configured to establish a link with the remote locating service 18 also when the link is initiated by the remote locating service 18.

In block 52, the medical device 12 is configured to perform functions necessary for the ALI-capable system 10 to identify the location of the medical device 12. This is an optional step because, as described previously, the ALI-capable system 10 identifies the location of the medical device 12, not necessarily based on handset-based technologies but maybe based on network-based technologies. Specifically, if the particular embodiment of the ALI-capable system 10 is such that the data communicator 14 is configured to self-identify its location (and hence the location of the medical device 12), then block 52 is performed. On the other hand, in another embodiment of the ALI-capable system, the location of the medical device 12 may be determined by the overall communication network 16 (e.g., using TDOA technology) without having the data communicator 14 perform any particular ALI functions other than being turned on and transmitting/receiving signals to/from the network 16. In such a case, block 52 will be skipped.

Next in block 53, the medical device 12 may be configured to perform any predetermined function. For example, the medical device 12 may obtain various types of information, perform self-test, etc., and transmit the resulting data to the remote locating service 18, autonomously upon establishment of the link to the remote locating service 18. As a specific example, when a link to the remote locating service 18 is automatically established upon activation of the medical device 12 in the block 51, a signal indicating that the medical device 12 has been activated is transmitted to the remote locating service 18. The block 53 corresponds to the blocks 38 and 39 of FIG. 2.

In block 54, the mode of operation of the medical device 12 may transition to that of two-way speaker phone so that a user of the medical device 12 and a person at the central locating service 18 can verbally communicate with each other. Other modes of communication, for example, by text messaging and/or graphical messaging, are also possible according to conventional means.

In block 55, the controller 23 of the medical device 12 determines if there is a request signal sent from the remote locating service 18. A request signal may request various types of information (status, condition, self-test results, etc., of the medical device 12) or functions (e.g., software update). If a request signal is detected, in block 56, the medical device 12 receives and processes the request signal. In other words, the medical device 12 obtains the requested information or performs the requested functions. The block 56 corresponds to the block 37 of FIG. 2. Thereafter in block 57, the medical device 12 is configured to transmit data resulting from the block 56 to the remote locating service 18. The block 57 corresponds to the block 39 of FIG. 2.

After the block 57, or in the block 55 if no request signal from the remote locating service 18 is detected, in a next block 58, the controller 23 of the medical device 12 determines if a link break-off signal is detected. A break-off signal may be initiated from the remote locating service 18, or may be initiated within the medical device 12 either manually or autonomously. Specifically, a break-off signal may be initiated manually, by the user of the medical device 12 actuating a switch (not shown), or automatically upon occurrence of certain triggering events associated with the operation of the medical device 12, for example deactivation (turning off) of the medical device 12.

As apparent from FIG. 5, in accordance with the present invention, an emergency caregiver operating the medical device 12 and a person operating the remote locating service 18 can freely communicate with each other verbally or via textual or graphical messaging while the two devices are linked together. For example, the caregiver can describe the condition of a patient via the user interface 25 (microphone, input keys) to the central dispatch listening to a speaker or watching a user interface display of the remote locating service 18. The central dispatch, in turn, may provide emergency situation coaching, on how to administer cardiopulmonary resuscitation (CPR) or use an AED device, to the caregiver listening to or watching the user interface 25 (speaker, display) of the medical device 12. Additionally, the central dispatch may send any pre-stored patient data (e.g., the patient's medical history) to the medical device 12 for display to the caregiver operating the medical device 12.

The foregoing has described various operations of a wireless ALI-capable system of the present invention in case of emergency, i.e., when the medical device 12 is actually deployed to treat a patient requiring immediate medical attention. The wireless ALI-capable system of the present invention, however, is further capable of monitoring the condition or status of one or more medical devices in nonemergency settings. This is advantageous because, for example, the American Heart Association recommends that AEDs be widely placed in the hands of trained, nontraditional rescuers, such as police, security guards, and family members of patients at high risk for cardiac arrest. Public access defibrillation (PAD) programs place AEDs in homes, police cars, worksites, and public gathering places under the supervision of licensed physicians, so as to increase the accessibility of AEDs and hence the chance of successfully resuscitating a patient having cardiac arrest. However, such programs will work only if a plurality of widely placed AEDs are well maintained at all times. A wireless ALI-capable system of the present invention in accordance with the present invention is adapted to meet this goal by using the remote locating service to centrally monitor a plurality of medical devices to check for any defects or faults requiring servicing or other attention.

Specifically, FIG. 6 is a flow diagram illustrative of the operation of one embodiment of the wireless ALI-capable system 10 of the present invention, wherein the central locating service 18 monitors one or more medical devices 12. In block 62, the medical device 12 is configured to initiate a communication link to the remote locating service 18. The link is established so that the medical device 12 can transmit information regarding its status, condition and/or self-test results to the remote locating device 18. As described above, though only one medical device 12 is shown in FIG. 1, a plurality of medical devices can be provided and configured to each initiate a link to the remote locating service 18, as will be appreciated by those skilled in the art. In this embodiment, the remote locating service 18 can be operated by a person in charge of remotely and centrally monitoring one or more medical devices 12, perhaps fire station personnel in charge of maintaining a plurality of medical devices (e.g., AEDs) placed throughout its jurisdiction. The link may be established manually, for example, by a user operating the medical device 12 calling a number associated with the remote locating service 18 using the wireless data communicator 14.

Alternatively, the link may be established periodically according to a clock (not shown) coupled to the controller 23 of the medical device 12 and also according to a predefined schedule stored in the memory 46 (FIG. 3). For example, the controller 23 may be configured to initiate a link to the remote medical device 18 annually or semiannually to prompt a person operating the remote locating device 18 to service the medical device 12.

Further alternatively, the controller 23 may be configured to autonomously initiate a link upon occurrence of various triggering events that are expected to occur according to a certain time schedule stored in the memory 46, for example: (1) a component of the medical device has expired (e.g., usable life of batteries or electrodes of an AED has expired); (2) a component of the medical device is nearing its expiration; and/or (3) the designated user of the medical device needs to be retrained in the use and operation of the medical device (e.g., typically, a nontraditional rescuer needs to be trained in the proper use of an AED at least once a year). The triggering events may also be unscheduled or unpredictable occurrences associated with the medical device 12, for example: (4) the medical device is malfunctioning, as determined based on periodically conducted self-tests (e.g., the voltage level of the power source 41 in FIG. 3 is too low); (5) the medical device is stolen (e.g., by constantly monitoring a local parameter, such as an ambient temperature, determining that the medical device has been removed from its assigned location if the parameter falls outside a predetermined range); (6) the medical device is activated (turned on); and/or (7) the medical device is deactivated (turned off). Any other events that require servicing or other forms of attention may also be used to trigger initiation of a link between the medical device 12 and the remote locating service 18.

In block 63, as before, the ALI-capable system 10 identifies the location of the medical device 12 that initiated the link to the remote locating service 18. In block 64, the location identified in the block 63 is received and preferably displayed on the remote locating service 18. Furthermore, any signals indicating the condition or status of the medical device, for example, any of the link-initiating triggering events described above, may also be transmitted to and displayed on the remote locating service 18. Thus, an operator of the remote locating service 18 can determine the type of service required with respect to the particular medical device 12. In one embodiment, the control unit 27 of the remote locating service 18 is configured to produce an audible or visual alarm signal via the user interface 19 upon receipt of any of these link-initiating triggering events signals. The alarm signal will alert and prompt the operator of the remote locating service 18 to take an appropriate action based on the information received in the remote locating service 18. For example, the operator may contact and direct the person responsible for the medical device 12 to bring the medical device to an authorized facility for necessary servicing, or send a service agent to the medical device 12 to perform necessary servicing.

FIG. 7 is a flow diagram illustrative of yet another operation of the ALI-capable system 10 of the present invention, wherein the remote locating service 18 is used to centrally monitor one or more medical devices 12. In block 65, the remote locating service 18 initiates a communication link to the medical device 12 via the communication network 16. As before, though only one medical device is illustrated in FIG. 1, the remote locating service 18 can be configured to link and communicate with multiple medical devices 12. In this configuration, the control unit 27 of the remote locating service 18 may be adapted to periodically "poll" multiple medical devices daily, weekly, monthly, etc., depending on the number of medical devices and the capacity of the communication network 16.

In a next block 66, the remote locating service 18 transmits an inquiring request signal to the medical device(s) 12 to provide status/condition information, perform self-tests, change software configuration, or perform various other functions (similarly to the block 36 of FIG. 2). In an embodiment wherein the medical device 12 is an AED, the requested status and condition information may include battery charge level, configuration parameters, and/or internal state (e.g., off, on, or charging).

In a next block 67, the medical device 12 receives the request signal from the remote locating service 18 and extracts and executes instructions included in the request signal (corresponding to the block 37 of FIG. 2). Next in block 68, the medical device 12 transmits the resulting data, e.g., the results of the requested process or requested information, to the remote locating service 18 (corresponding to the block 39 of FIG. 2). As before, the transmitted resulting data are then received and preferably displayed on the user interface 19 of the remote locating service 18, so that the operator of the remote locating service 18 can take an appropriate action in response.

Also as before, in block 69, the wireless ALI-capable system 10 identifies the location of the medical device 12, and in block 70 the identified location is received and preferably displayed in the remote locating service 18. It should be understood that the location identification steps of the blocks 69 and 70 need not occur after the blocks 66–68, and instead may occur before or even concurrently with the blocks 66–68.

While the various embodiments of the ALI-capable system of the present invention have been illustrated and described, it will be appreciated that various changes can be made therein without departing from the spirit and scope of the invention.

The embodiments of the invention in which an exclusive property or privilege is claimed are defined as follows:

1. A wireless automatic location identification (ALI) capable system for locating a portable medical device, comprising:
   a medical device having a wireless data communicator;
   a wireless communication network; and
   a remote locating service;
   wherein, when the medical device is linked to the remote locating service over the communication network, at least one of the wireless data communicator and the wireless communication network utilizes an ALI technology to determine the location of the medical device and provides information identifying the location of the medical device to the remote locating service.

2. The system of claim 1, wherein the wireless data communicator comprises a cellular phone.

3. The system of claim 1, wherein the wireless data communicator identifies the location of the medical device based upon a handset-based ALI technology.

4. The system of claim 1, wherein the wireless communication network identifies the location of the medical device based upon a network-based ALI technology and the link between the wireless data communicator and the remote locating service over the communication network.

5. The system of claim 1, wherein the ALI-capable system utilizes a handset-based ALI technology in part and a network-based ALI technology in part.

6. The system of claim 1, wherein the medical device comprises an external defibrillator.

7. The system of claim 1, wherein the medical device is configured to automatically link itself to the remote locating service over the network upon occurrence of a predetermined triggering event.

8. The system of claim 7, wherein a signal indicative of the triggering event is automatically transmitted to the remote locating service.

9. The system of claim 8, wherein the remote locating service is configured to emit an alert signal upon receipt of the signal indicative of the triggering event.

10. The system of claim 7, wherein the medical device comprises an external defibrillator, and the triggering event is selected from the group consisting of: (1) activation of the external defibrillator; and (2) application of electrodes of the external defibrillator on a patient.

11. The system of claim 1, wherein the medical device is configured to transmit a signal indicative of a status of the medical device via the wireless data communicator to the remote locating service.

12. The system of claim 11, wherein the medical device is configured to periodically link itself to the remote locating service to transmit the status of the medical device to the remote locating service.

13. The system of claim 11, wherein the status of the medical device is transmitted in a signal upon receiving a request from the remote locating service.

14. The system of claim 11, wherein the medical device comprises a defibrillator, and the status of the medical device transmitted in a signal comprises a self-test result.

15. The system of claim 1, wherein the medical device is configured to transmit or receive patient data via the wireless data communicator to or from the remote locating service.

16. The system of claim 1, wherein the remote locating service is associated with an emergency phone number.

17. The system of claim 1, wherein the remote locating service comprises a display for displaying the location of the medical device.

18. The system of claim 1, wherein the medical device and the remote locating service are adapted to transceive audio signals.

19. The system of claim 1, wherein the medical device and the remote locating service are adapted to transceive text and graphical messaging.

20. The system of claim 3, wherein the wireless data communicator includes a global positioning system (GPS) receiver, and uses the GPS receiver to identify the location of the medical device.

21. The system of claim 4, wherein the wireless communication network utilizes at least one of a time difference of arrival technique and a timing advance technique to locate the medical device.

22. A method of locating a portable medical device, the method comprising:
   providing a wireless automatic location identification (ALI) capable system comprising a medical device having a wireless data communicator, a wireless communication network, and a remote locating service;
   linking the medical device to the remote locating service over the communication network;
   utilizing an ALI technology to identify the location of the medical device; and providing information identifying the location of the medical device to the remote locating service.

23. The method of claim 22, wherein the location of the medical device is identified based upon a handset-based ALI technology.

24. The method of claim 22, wherein the location of the medical device is identified based upon a network-based ALI technology and the link between the medical device and the remote locating service over the communication network.

25. The method of claim 22, wherein the ALI-capable system utilizes a handset-based ALI technology in part and a network-based ALI technology in part.

26. The method of claim 23, wherein the location of the medical device is identified according to a global positioning system.

27. The method of claim 24, wherein the location of the medical device is identified according to at least one of a time difference of arrival technique and a timing advance technique.

28. A medical device capable of being located by a remote locating service, the medical device comprising:
    circuitry for operation of the medical device; and
    a wireless data communicator for establishing a wireless communication link between the medical device and a remote locating service;
    wherein when the medical device is linked to the remote locating service, the wireless data communicator automatically identities the location of the medical device according to an automatic location identification (ALI) standard, and provides information identifying the location of the medical device to the remote locating service.

29. The medical device of claim 28, wherein the wireless data communicator comprises a cellular phone.

30. The medical device of claim 28, wherein the wireless data communicator utilizes a handset-based ALI technology to identify the location of the medical device.

31. The medical device of claim 28, wherein the medical device is an external defibrillator.

32. The medical device of claim 28, wherein the wireless data communicator is configured to automatically establish the wireless communication link between the medical device and the remote locating service over the wireless communication network upon occurrence of a predetermined triggering event.

33. The medical device of claim 32, wherein a signal indicative of to triggering event is automatically transmitted to the remote locating service.

34. The medical device of claim 30, wherein the wireless data communicator includes a global positioning system (GPS) receiver, and utilizes the GPS receiver to identify the location of the medical device.

35. A method of locating a portable medical device, the method comprising:
    establishing a link between the portable medical device and a remote locating service;
    automatically locating the portable medical device using a wireless automatic location identification (ALI) capable system; and
    receiving the identified location of the portable medical device in the remote locating service.

36. The method of claim 35, wherein the link between the portable medical device and the remote locating service is established periodically.

37. The method of claim 35, wherein the link between the portable medical device and the remote locating service is established automatically upon occurrence of a triggering event in the portable medical device.

38. The method of claim 37, wherein a signal indicative of the triggering event is transmitted to the remote locating service.

* * * * *